United States Patent [19]

Pearlman

[11] Patent Number: 5,602,891
[45] Date of Patent: Feb. 11, 1997

[54] IMAGING APPARATUS AND METHOD WITH COMPENSATION FOR OBJECT MOTION

[75] Inventor: Justin D. Pearlman, Brookline, Mass.

[73] Assignee: Beth Israel, Boston, Mass.

[21] Appl. No.: 558,019

[22] Filed: Nov. 13, 1995

[51] Int. Cl.$^6$ .................................................. G01N 23/02
[52] U.S. Cl. .............................. 378/62; 378/901; 378/8; 250/363.01; 250/369; 364/413.23
[58] Field of Search .................... 250/363.01, 363.02, 250/363.04, 369, 370.08, 370.09, 370.1, 370.11; 378/8, 62, 901; 364/413.14, 413.23

[56] References Cited

U.S. PATENT DOCUMENTS

| | | | |
|---|---|---|---|
| 4,450,478 | 5/1984 | Ledley | 378/98.12 |
| 4,663,591 | 5/1987 | Pelc et al. | 324/309 |
| 4,672,651 | 6/1987 | Horiba et al. | 378/62 |
| 4,712,560 | 12/1987 | Schaefer et al. | 128/653 |
| 4,719,585 | 1/1988 | Cline et al. | 364/518 |
| 4,729,098 | 3/1988 | Cline et al. | 364/414 |
| 4,777,957 | 10/1988 | Wehrli et al. | 128/653 |
| 4,796,635 | 1/1989 | Dumoulin | 128/653 |
| 4,800,889 | 1/1989 | Dumoulin et al. | 128/653 |
| 4,858,128 | 8/1989 | Nowak | 364/413.13 |
| 4,926,124 | 5/1990 | Le Roux | 324/309 |
| 4,947,120 | 8/1990 | Frank | 324/309 |
| 4,984,157 | 1/1991 | Cline et al. | 364/413.13 |
| 4,985,834 | 1/1991 | Cline et al. | 364/413.12 |
| 4,995,394 | 2/1991 | Cline et al. | 128/653 |
| 5,049,746 | 9/1991 | Ito | 250/327.2 |
| 5,150,427 | 9/1992 | Frazee et al. | 382/48 |
| 5,210,415 | 5/1993 | Ito | 250/327.2 |
| 5,251,128 | 10/1993 | Crawford | 364/413.19 |
| 5,271,055 | 12/1993 | Hsieh et al. | 378/95 |
| 5,319,693 | 6/1994 | Eberhard et al. | 378/19 |
| 5,361,291 | 11/1994 | Toth et al. | 378/12 |
| 5,383,119 | 1/1995 | Tam | 364/413.19 |
| 5,383,231 | 1/1995 | Yamagishi | 378/15 |
| 5,390,111 | 2/1995 | Tam | 364/413.14 |
| 5,390,112 | 2/1995 | Tam | 364/413.15 |
| 5,390,226 | 2/1995 | Tam | 378/19 |
| 5,485,371 | 1/1996 | Ito et al. | 364/413.23 |

FOREIGN PATENT DOCUMENTS 2700039 7/1994 France.

OTHER PUBLICATIONS

Belohlavek, M., et al., "Three–Dimensional Ultrasound Imaging of the Atrial Septum: Normal and Pathologic Anatomy," *J Am Coll Cardiol*, 22(6):1673–1678, (Nov. 15, 1993).

Greenleaf, J. F., et al., Mayo Clinic Proceedings, "Multidimensional Visualization in Echocardiography: An Introduction," *Mayo Clin Proc*, 68:213–220, (Mar. 1993).

Sehgal, C. M., et al., "Ultrasound Transmission and Reflection Computerized Tomography for Imaging Bones and Adjoining Soft Tissues," IEEE 1988 Ultrasonics Symposium, pp. 849–852.

(List continued on next page.)

*Primary Examiner*—David P. Porta
*Assistant Examiner*—David Vernon Bruce
*Attorney, Agent, or Firm*—Hamilton, Brook, Smith & Reynolds, P.C.

[57] ABSTRACT

An apparatus and method for generating a data set representation of an object or tissue are described. Two image representation data sets for the object or tissue are generated by a CT or MRI scan or other known imaging process. The second data set is preferably generated with enhanced contrast between background tissue and the target tissue of interest, e.g., blood vessels, such as by the injection of a vascular contrast enhancing agent. The first data set is viewed as the union of plural data value neighborhoods, with each neighborhood preferably surrounding a central data value. Each data value of the second data set is compared to a neighborhood in the first data set. If a data value in the second data set is incompatible with the neighborhood, then it is concluded that the data value in the second data set is representative of contrast-enhanced target tissue and is therefore used to generate the final image data set of the target tissue.

44 Claims, 8 Drawing Sheets

OTHER PUBLICATIONS

Ylitalo, J., et al., "Coherent High–Resolution Ultrasound Reflection Mode CT Imaging," IEEE 1986 Ultrasonics Symposium, pp. 833–835.

Hale, J. D., et al., "MR Imaging of Blood Vessels Using Three–Dimensional Reconstruction: Methodology," 157(3):727–733, (Dec. 1985).

Chen, C. W., et al., "Surface Modeling in Heart Motion Analysis," SPIE vol. 1610, *Curves and Surfaces in Computer Vision and Graphics II*, (1991).

Bolson, E. L. et al., "Quantification of Asynchronous Displacement of Heart Borders," *IEEE*, pp. 613–616, (1991).

Ren, Z., et al., "Analysis and Characterization of the Left Ventricular Wall Motion by Means of 3D–Models," *IEEE*, pp. 643–646 (1988).

Boesiger, P., et al. "Visualization and Quantification of the Human Blood Flow by Magnetic Resonance Imaging," *J. Biomechanics*, 25(1):55–67, (1992).

Watanabe, T., et al., "Computer Simulation of Ventricular Wall Motion Using the Finite Element Method," *Radiation Medicine*, 6(4):165–170, (1988).

Spickler, E., et al., "Approaches to MR Angiography," *Computerized Medical Imaging and Graphics*, 12(4):211–217, (1988).

"NMR –A perspective on imaging," General Electric, pp. 3–30, No Date.

Pearlman, J. D., et al., "Tissue Characterization," Chapter 41, *Principles and Practice of Echocardiography*, pp. 1264–1287, (1994).

|   | 1 | 2 | 3 | 4 | 5 |
|---|---|---|---|---|---|
| 1 | 1 | 2 | 3 | 5 | 2 |
| 2 | 2 | 4 | 7 | 1 | 5 |
| 3 | 4 | 3 | 6 | 1 | 9 |
| 4 | 2 | 4 | 1 | 1 | 1 |
| 5 | 3 | 1 | 2 | 2 | 3 |

|   | 1 | 2 | 3 | 4 | 5 |
|---|---|---|---|---|---|
| 1 |   | 3 | 5 | 5 |   |
| 2 |   | 7 | 7 | 7 |   |
| 3 |   | 6 | 6 | 9 |   |
| 4 |   | 4 | 4 | 1 |   |
| 5 |   | 3 | 3 | 3 |   |

FIG. 10B

|   | 1 | 2 | 3 | 4 | 5 |
|---|---|---|---|---|---|
| 1 |   |   |   |   |   |
| 2 |   | 7 | 7 | 9 |   |
| 3 |   | 7 | 7 | 9 |   |
| 4 |   | 6 | 6 | 9 |   |
| 5 |   |   |   |   |   |

FIG. 10C

IMAGING APPARATUS AND METHOD WITH COMPENSATION FOR OBJECT MOTION

BACKGROUND OF THE INVENTION

The present invention relates to imaging systems such as x-ray equipment, computed tomography imaging apparatus and magnetic resonance imagers, and more particularly, to techniques for processing image data to eliminate the effects of movement of the patient between multiple images.

In some computed tomography (CT) systems an x-ray source projects a fan-shaped beam which is collimated to lie within an X-Y plane of a Cartesian coordinate system, termed the "imaging plane." The x-ray beam passes through the object being imaged, such as a patient undergoing diagnostic evaluation, and impinges upon an array of radiation detectors. The intensity of the transmitted radiation is dependent upon the attenuation of the x-ray beam by the patient, and each detector produces a separate electrical signal that is a measurement of beam attenuation along a specific ray path. The attenuation measurements from all the detectors are acquired separately to produce the transmission profile.

The source and detector array mounted on a gantry in a common type of CT system are rotated around the patient so that the angle at which the x-ray beam intersects the patient constantly changes. The gantry may stop or continue to move as the measurements are being made. The images produced from the scan data correspond to a stack of two-dimensional slices taken through the patient.

Typical CT systems may be operated in either the axial mode or the helical scan mode. In the typical axial mode, the patient being imaged remains stationary during each scan. The patient may be moved between rotations in order to obtain different slices through the patient. In the conventional helical scan mode, the gantry with the x-ray source and detector array revolves continuously while the patient is translated through the imaging plane. The data are processed subsequently to form the desired image planes through the patient.

The resultant set of projections from a scan are used to reconstruct images which reveal the anatomical structures at the position of each slice taken through the patient. The prevailing method for image reconstruction is referred to in the art as the filtered back-projection technique. This process converts the attenuation measurements from a scan into an array of integers called "CT numbers" or "Hounsfield units", which are used to control the brightness of a corresponding pixel on a cathode ray tube display.

In many imaging applications, it is desirable or necessary to collect scan data sets for two distinct images of the same subject. For example, in medical applications such as angiography, at least two x-ray image data sets are commonly obtained for a region of tissue being analyzed such as the patient's head. Before the second data set is obtained, a vascular contrast-enhancing agent is injected into the patient. In principal, a process known as image subtraction, or specifically digital image subtraction, can then be applied to the two data sets to "subtract" one image data set from the other to remove background features common to both data sets such as bone and soft tissue, leaving an image data set for only the target tissue of interest, namely, the blood vessels in the region of tissue.

In reality however, the two image data sets generally differ by more than simply the enhanced contrast of the blood vessels. Movements in the region of tissue between images caused by pulsation of vessels, muscle contractions, etc., cause shifts in position of both background tissue and the target tissue of interest. Because of the shifts in position, a simple straightforward subtraction of the image data sets does not produce an accurate image of the target tissue.

Some prior imaging systems and processes have made attempts at reducing the effects of patient movement between images. One of these involves identifying certain "fiduciary points" and tracking their movement between images. For example, when imaging the head of a patient, fiduciary points may include data points defining the tip of the noise, earlobes, teeth, etc. The movement of these fiduciary points between images is identified, and an estimate of the movement of other points between the fiduciary points is generated using interpolation.

This method can produce inaccurate results. The fiduciary points are selected because they are easy to identify in the image data sets, not necessarily because their movement is representative of the movement of all points in the tissue. The points in the tissue between the fiduciary points can move very differently than the fiduciary points themselves. Thus, interpolating between fiduciary points will not produce an accurate measure of the movement of other points in the tissue.

Thus, there is a need for an object or tissue imaging system and method which can accurately compensate for movement of the object or tissue between image data set acquisition.

SUMMARY OF THE INVENTION

The present invention is directed to an imaging apparatus and method for generating an image data set representation of target tissue such as blood vessels in a region of tissue from two data set representations of the region obtained under two different conditions. In the second image data set, for example, contrast between the target tissue and the background tissue in the region is enhanced such as by injection of a vascular contrast-enhancing agent into the blood vessels in the region. A new third or final data set is formed which is approximately representative of the difference between the first and second data sets corrected for motion in the region of tissue between acquisition of the first and second data sets and, therefore, is representative of contrast-enhanced target tissue. Data values of the first data set representation can be grouped into plural neighborhoods of data values. Data values of the second data set representation are compared with corresponding neighborhoods of data values of the second data set representation to distinguish data values of the second data set that are representative of the target tissue from those that are representative of the background tissue. A data set representation of the target tissue is generated using data values associated with the target tissue.

The data values used to represent the images can be representative of any of several physical attributes of the images. For example, each data value can represent the intensity of a single pixel in the image. Also, each data value can be a vector that represents attributes of a group or neighborhood of pixels. For example, one data value component can represent peak, average or total intensity over a neighborhood of pixels that surround a central pixel. Another data value component can represent image texture. For example, that data value component can contain information related to the run length of a particular range of values, i.e., dark or bright. Data values can also be used to represent intensity gradients for neighborhoods of pixels. Data values can also store information regarding statistical moments of the pixel intensity values for a neighborhood of pixels, including mean and variance of pixel intensities within the neighborhood.

In one embodiment, the image data sets can effectively be viewed as the union of neighborhoods around each image pixel. The data values describing image attributes in each neighborhood of the first image data set, such as the neighborhood peak pixel intensity, intensity gradients and/or intensity mean and variance, can be used to generate summary data for the tissue within that neighborhood. Corresponding data values in the second image data set are then analyzed to determine if they are compatible with the summary data for that neighborhood in the first image data set. If a data value is compatible with the corresponding neighborhood, then it is taken to be representative of background tissue since the corresponding neighborhood is a neighborhood in the first data set without any target enhancement. If, on the other hand, the data value is incompatible with the neighborhood, then it is taken as representative of enhanced target tissue and is used to generate the new data set representation of the target tissue.

In another embodiment of the invention, the comparison between derived data values of the two image data sets involves a point-by-point comparison of the two derived image data sets. In this embodiment, data values for the first image data set are stored in an array. The second data set is scanned one value at a time searching for values which correspond to the data values in the first data set. Values in the second data set which do not correspond to data values in the first data set are used to generate the new image data set for the target tissue.

In one embodiment, the first image data set is viewed as the union of plural neighborhoods whose attributes are defined by data values computed from the image data set. The data values are used to generate the summary data for each neighborhood. The second image set is analyzed with respect to each value, with each value being compared to corresponding neighborhood summary data of the first image data set. When a value is determined to be compatible with a neighborhood, it is taken as representative of background tissue because the value appears to be present in both image data, sets. A displacement between the location of the value in the second data set and its closest match value in the corresponding neighborhood of the first image data set is also preferably computed. The displacement indicates the minimum amount the tissue represented by the value present in both image sets must have moved between image sets. The match and the displacement need not be observed as discrete values but rather may be computed on a continuum as floating point values supported by the neighborhood descriptors. If the value is not compatible with a neighborhood, it is concluded that the value represents enhanced target tissue, so it is included to generate the new image data set.

In one embodiment, the size and shape of each pixel data value neighborhood are determined by the amount of displacement which the subject tissue can be expected to experience. If each portion of tissue represented by a single value can be expected to move only the distance defined by a single image pixel, then a neighborhood around each pixel value can be a cube-shaped volume defined by 26 pixel values surrounding each central pixel value. The neighborhood can also be a spherical region surrounding the pixel value or it can have an asymmetrical configuration, such as a rectangular solid.

By comparing the first and second image data sets in terms of neighborhoods of image pixel data values, the method and apparatus of the invention compensate for the effects of tissue movement between images. The neighborhoods define characteristics of regions or volumes of tissue, rather than simply single point locations of tissue intensity values. As such, the neighborhoods allow identification of tissue that has been subjected to motions that are not strictly rigid and linear but, instead, are elastic and non-uniform, which are the more common types of movements occurring in the human body.

Thus, even if the tissue represented by a data value has moved in a manner which is not easily characterized, the tissue can still be identified in the second data set based on the characteristics of a group or neighborhood of pixel data values. Therefore, the effects of non-linear elastic motions such as vessel pulsations, swallowing, etc. that result in the stretching, shifting, compressing and/or rotating of different tissue regions in an image can be compensated for in the final image data set.

In one preferred embodiment, each data value is actually a vector representing several items of data. For example, each vector can include x, y and z cartesian position coordinates and observation data for a pixel at those coordinates. The observation data can include, for example, the intensity of the pixel at that location, the mean, variance and/or standard deviation of the pixel intensities within the neighborhood, and/or the pixel intensity gradient for the pixel. When values in the second image data set are compared with neighborhood data values in the first image data set, the individual attributes for the corresponding vectors are compared.

In one preferred embodiment, a pairing vector can be computed for each data value (vector) in the second image data set determined to represent background tissue based upon these comparisons within the corresponding neighborhood in the first image data set. Each pairing vector can represent several quantities. One of the quantities is an error value representing the difference in observation values between the two vectors. For example, if the observation quantity in each vector is a pixel gradient, then the pairing vector contains a measure of the vector difference between gradients for the two compared vectors.

In one embodiment, the observation difference error value is the minimum such error computed between the value of the second image data set and each of the values in the neighborhood of the first image data set. That is, the comparison involves comparing the observation value for the vector in the second image data set with the observation values for each vector in the corresponding neighborhood of the first image data set. The error value in the pairing vector is equal to the lowest difference computed and, therefore, is a measure of the match between the data value of the second data set and a "best match" value in the corresponding neighborhood of the first data set. For example, where the observation value for each vector is pixel intensity, the observation error value in the pairing vector can be the difference in intensity between a value of the second data set and a best match intensity value in a corresponding neighborhood of the second data set.

In one embodiment, the neighborhoods in the first image data set are representative of a continuum of data values. In that embodiment, the best match need not be at a single discrete pixel value location. Instead, values between pixel values are interpolated to find the location of a best match value, even if that position location is at a fraction of a unit distance between pixel locations.

Another value represented by each pairing vector can be the displacement between the pixel represented by the value in the second image data set and the location of the best match pixel value in the corresponding neighborhood of first image data set. That is, the displacement portion of the pairing vector is the difference in position data between the two pixel values.

In one embodiment, if the error value of a pairing vector is below a certain threshold, then it is assumed that the pixel data value is present in both image data sets and is therefore representative of background tissue. In that case, the displacement portion of the pairing vector represents the amount of movement that the tissue represented by the pixel data value underwent between collection of the two image data sets.

After the entire second image data set is thus processed to compare values of the second data set with values of the first data set, a process for discriminating background tissue values from target tissue values for the new data set can be implemented. The process is used to distinguish background tissue values which may have moved between images from target tissue values which also may have moved.

Any of several discriminating approaches can be applied to the comparison data or pairing vector space to distinguish background values from target tissue values. One approach is to choose an error threshold and apply it to the observation difference or error portion of each pairing vector. Those values having pairing vectors with error data above the threshold are taken to be target tissue values. Values with error values below the threshold are taken to be background tissue values. In one embodiment, the threshold is selected according to the expected noise level present in the data values.

Alternatively, a pair of thresholds can be applied to the error data. Values having error data below the lower threshold are identified as background or old values, and those having error data above the higher threshold are identified as target or new values. Values having error data which fall between the two thresholds can be classified as equivocal or uncertain. These values can be processed further to associate them with either the new or old values depending upon reprocessing criteria applied to them as described below.

Another approach to discriminating background values from target values is a statistical approach. Under this approach, statistical measures such as the mean and standard deviation of the error values are computed. Values having a variation from the mean larger than a certain threshold number of standard deviations can be concluded to be target tissue values, and values within the threshold are determined to be background tissue values. In many imaging applications such as angiography, it is likely that the target tissue will occupy a very small percentage of the overall image represented by the second data set. In these applications, the threshold is set very high, e.g., two standard deviations, such that most of the values of the second data set are discarded. As in the previously described process, dual statistical thresholds can be selected to identify values having error data on the borderline between background and target. The dual thresholds allow values in the range between the thresholds to be identified as uncertain and requiring further processing.

In still another discriminating process, a certain percentage of all of the values are concluded to be background tissue values. For example, it can be a priori concluded based on the application, e.g., angiography, that some large percentage of the values in the second image data set, for example 95%, are representative of background tissue. In that case, the 95% of the values having the lowest pairing vector error values are discarded as representative of background tissue and the 5% with the largest error values are kept as target tissue values.

In another data discrimination approach, the error data in the pairing vectors is analyzed to locate a break in the error values that is representative of the natural break between background tissue and target tissue. Since in most physical applications the difference between background tissue and target tissue is not a continuum, but rather, is a distinctive change in pixel intensity value, the pairing vector data can essentially be divided into two groups, i.e., background tissue and target tissue data. Once the natural break in error values is identified, data values having error data values above the error value at the break are concluded to be representative of target tissue, and those below the break are taken as background tissue. In this approach, a histogram can be generated to group the error values. By analyzing the histogram, the break between background and target tissue error values can be readily identified.

Another discrimination approach referred to herein as "mixture modeling" involves fitting curves to the error data. Under the mixture modeling approach, it is assumed that the error data represents two distributions, one for data values that are present in both data sets but may have been slightly altered by noise and/or motion and a second set of data representing new contrast-enhanced data points found in only the second data set. It is further assumed that each distribution can be represented by its own individual curve. A curve fitting approach such as maximum likelihood estimation (MLE) is then applied to the data to compute two curves which when combined into a single curve yield a best fit curve for the data. The resulting two curves then define the breakpoint between background tissue data values and target tissue values. In one embodiment, the misclassification rates of background as target tissue and of target tissue as background are calculated as a function of the two curves and the breakpoint. The breakpoint is then selected so as to provide a set error rate for one or both of these parameters or to minimize their weighted sum.

In an alternative preferred embodiment, the comparison process between the second image data set and the first image data set can be made very efficient while final image fidelity is maintained. In this alternative process, it is assumed that the contrast enhancement results in generating target tissue pixel values that are brighter (or darker) than the background tissue pixel values. Hence, the comparison process involves determining whether a pixel in the second image data set is brighter than the brightest pixel in the corresponding neighborhood of the first image data set, assuming that the contrast enhancement process brightens enhanced tissue.

Under this process, each value in the second image data set is compared to its corresponding neighborhood in the first image data set. If the value in the second image data set indicates a pixel intensity brighter than the brightest pixel value in the corresponding neighborhood of the first image data set by a selected threshold, then it is concluded that the value of the second image data set corresponds to contrast-enhanced target tissue. If the intensity value of the second data set does not exceed the maximum intensity value of the corresponding neighborhood of the first data set by the threshold, then it is considered to be representative of background tissue. In this approach, dual thresholds can also be set to identify uncertain values. This approach simplifies analysis because a comparison array of local maxima can be computed quite efficiently and then the values to be kept for the final image set are selected by a simple comparison.

As in the approach described above, in this alternative approach, a pairing vector can also be computed for each value in the second image data set. Again, the pairing vector can include data describing the displacement between the location of the value in the second image data set and the location of its best match value within the corresponding neighborhood of the first image data set. For a value without a discrete value match, the displacement data can be interpolated from the displacement data of neighboring values in the neighborhood. Another data value contained in the pairing vector can be the intensity observation difference or error between the intensities of the value in the second image data set and its best match value in the first image data set. Again, interpolation between values in the neighborhood can be used to create an intensity continuum effect within the neighborhood of the first image data set.

In a preferred embodiment, part of the process of discriminating background values from target values involves generating a mask which, when applied to the data values of the second data set, causes values representative of background tissue to be discarded and causes data values representative of target tissue to be saved for the final data set. In one embodiment, the mask is an array of trinary numbers, each of which is assigned to a data value of the second data set. Each data value can preferably be assigned one of three possible numbers. For example, a data value identified as being representative of background tissue can be assigned the number −1, values representative of target tissue can be assigned the number +1, and data values marked as uncertain or equivocal can be assigned a value 0. Hence, for all locations of the second data set, a mask number marks whether the location was changed by the contrast (+1) or was present in the first data set albeit at a shifted location (−1), or may require further analysis to make a final determination (0).

The mask thus generated can then be applied to the data of the second data set to generate a new data set which can then be used to create an image of the target tissue. Alternatively, an interim reclassification or filtering step can be applied to the mask to further classify uncertain (0) locations as being either background (−1) or target (+1). Reclassifying each 0 location as either +1 or −1 can involve application of one or more of several classification criteria which are based upon known physical attributes of tissue and tissue movement. For example, a 0 location can be reclassified as a +1 if the displacement vector associated with the 0 location has a negative vector dot product with the displacement vector for a neighboring −1 location. The negative dot product indicates that the two displacement vectors point in opposite directions. This is an inconsistency because such motion would disrupt the tissue. To maintain characterization of the tissue consistent with known physical tissue movement constraints, the 0 location is reclassified as a +1 to indicate that it must actually be associated with enhanced target tissue that was not present in the first image data set instead of background tissue that has moved. A 0 can also be reclassified as a −1 if it is entirely isolated, i.e., there are no +1 locations nearby. Further, a 0 can be reclassified as +1 if it establishes continuity in the tissue represented by the data, i.e., its inclusion creates a connection between two +1 locations from the first pass of the data that were separated by the 0.

In a preferred embodiment, after the data values of the second data set are classified as background, target or unknown and each is assigned a number −1, 0 or +1, the invention can perform a consistency check on the data to ensure that the final image data set for the target tissue is in accordance with certain predetermined tissue movement constraints. In this embodiment, after the trinary number array is defined, the consistency check is performed to identify tissue movements defined by the data which would violate known physical tissue movement constraints. For example, in a manner similar to the process used to reassign 0 numbers to +1, a dot product can be computed between displacement vector data of adjacent pixel values. A negative dot product indicates that the tissue regions identified by the data values have crossed over one another between images. Such data points are flagged by the consistency check as requiring further analysis, since tissue typically does not undergo such movement. The further analysis may result in reclassification of the pixel values. For example, if the adjacent values are both identified as background (−1), one of them may be reclassified as target tissue (+1) since the indication of impossible tissue movement suggests that one of the values is actually indicative of contrast-enhanced data that was not present in the first data set and was mischaracterized as background on the first pass through the data.

Also, one of the values can be determined upon reanalysis during the consistency check to be representative of both target tissue and background tissue. That is, one of the values may be located at the border between background tissue and target tissue. In that case, the intensity of the region of tissue represented by that value is an average intensity for the region which is a lower value than would be present if the entire region were filled with contrast-enhanced target tissue. This is referred to herein as a "partial volume effect." As a result of the effect, the data value at that point of the tissue may be so reduced by averaging such that it is identified as background and is assigned a −1 value. Upon concluding that the partial volume effect has caused a misclassification such as by examining several adjacent pixel values to identify a border, the misclassified value can be reclassified as target tissue (+1) such that it can be included in the final target tissue data set.

Other processes of reanalyzing data values of the final image data set can also be performed to compensate for the partial volume effect. For example, the final image data set can be reanalyzed to identify the borders of the target tissue such as by identifying groups of +1 values adjacent to groups of −1 or 0 values. In the original comparison scan through the data, where a bright (high intensity) pixel value labelled +1 in the second image data set bordered a darker pixel value labelled −1, the darker pixel value would have been excluded from the final image data set. However, during reanalysis, to compensate for the partial volume effect, it can be assumed that the darker bordering pixel value actually includes some data for the target tissue and some data for the background tissue. These bordering pixel values can be added to the final image data set to improve the quality of the image at the target tissue borders. Even if the bordering value actually includes no target tissue information, inclusion of the value in the final image data can be useful because it does not obscure the pure target and it improves the accuracy of subsequent intensity gradient calculations of the surface normal for rendering.

The partial volume effect also manifests itself where a very thin piece of target tissue such as a thin blood vessel is completely contained within a single region of tissue represented by a single pixel value. In this case, if the averaging effect of the representative pixel value lowers the intensity value to a point where it is concluded to represent background tissue, the thin blood vessel will be missed in the final image data set. In this case, pixel value gradient comparison between the second image data set and the first image data set assists in identifying such partial volume pixel values. While the partial volume pixel may not influence the best match or highest-intensity value of a neighborhood, it will most likely change the gradient vector for a neighborhood. This can be identified upon reanalysis. If such a gradient vector is located, its corresponding pixel value can be included in the final image data set, even though it was initially excluded due to its lower intensity. Alternatively, a "skeletonizing" analysis as described below can be performed to ensure connectivity between target tissue pixel values, where appropriate.

The skeletonizing analysis is another post-comparison analysis that can be performed by the present invention. It can be done to ensure connectivity of image features in the final representation. Under this process, it is assumed that target tissue such as a blood vessel will have some form of uninterrupted path throughout the region of tissue. The image skeletonizing process involves examining each pixel value identified as representing target tissue and ensuring that it has at least one adjacent pixel value also identified as representative of target tissue. Where there is an interruption in target tissue pixel values, values for pixels between opposite sides of the interruption can be taken as being representative of target tissue and can be added to the target tissue image data set, even though in the initial comparison process they were excluded. This may involve reclassifying a 0 or −1 value as a +1 value.

This approach can also be used to compensate for the partial volume effect as noted above. For example, it may be that the interruption in target tissue pixel values was caused by the partial volume effect, i.e., that the region of interruption was only partially filled with enhanced target tissue and that the resulting reduced intensity values caused the associated values to be excluded. The skeleton approach causes the relevant partial volume pixel values to be included in the final target tissue image data set.

After the data values of the second data set are identified as being target tissue values (+1), background tissue values (−1) or uncertain (0), various image data sets can be generated to present images of the target tissue. One output consists of all points in the second data set in which the mask value is +1. Another consists of all the points in the second data set in which the mask value is +1. Additional images can include all values with a map number of 0 or +1. Other images include the nearest neighbors of all included points, i.e., points with a map number of −1 that are adjacent to a point that is 0 and/or +1. Inclusion of the nearest darker neighbor corrects for omission of partial volume elements. Inclusion of the immediate neighbors also improves gradient computations which estimate the surface and lighting condition for rendering the data as a three-dimensional object.

To further enhance the quality of the image generated from the final image data set, a subtraction process in accordance with the present invention can be carried out on the data after background values are discriminated from target values. The subtraction process involves eliminating from the total intensity of a data value identified as contrast-enhanced target tissue that portion of the total intensity that is due to the background tissue that was overlayed by the new contrast-enhanced tissue. In the subtraction process, each data value of the second data set identified as representing target tissue is analyzed individually by first pairing it with a derived interpolated counterpart value in the first image data set. The difference in the intensity for the two corresponding values represents the amount of enhancement introduced between images and, therefore, is also a representation of target tissue independent of the background tissue behind it. By subtracting the intensity of the first image value from that of the second image value, an intensity value for only the target tissue is obtained.

In this embodiment, the subtracted intensities replace those that were previously stored for the values of the final image data set. The result of this subtraction process is image data that gives a true indication of the actual intensity of the target tissue. Without subtraction, a very useful visual image of the target tissue can be obtained. However, subtraction can enhance that image to improve results of the process in several different ways. First, subtraction can eliminate from the final image data set data due to bone and bright artifacts which are found in both the first and second data sets and which would tend to obscure the target tissue data in the final target tissue image data set. Also, the subtraction process yields an indication of the amount of contrast enhancement that has taken place between the first and second image data sets. Where the contrast is enhanced by injection of a contrast agent into blood vessels and a series of images are obtained, time of arrival of the contrast enhancement can be determined. This provides a measure of blood vessel flow, perfusion and delivery rates. It can therefore indicate partial vessel blockage where contrast arrival time is longer than expected.

The tissue discrimination process of the invention allows abnormalities such as calcification of blood vessels to be identified. Calcification typically appears bright in CT imagery and therefore appears similar to contrast-enhanced blood vessels. Prior systems that compare data of a second data set to a threshold, instead of to the first data set, fail to discriminate contrast-enhanced blood vessel from calcification since both appear brighter than the threshold (in CT applications). In the present invention, because target tissue discrimination is accomplished by comparison of the contrast-enhanced data set with the non-contrast-enhanced data set, data values indicative of calcification will appear the same in both data sets and, therefore, will be eliminated from the target tissue image data set.

In the image formed from the data set generated by the present invention, calcification will appear as a blockage in the normal blood flow path. The user can interpret the image of the blockage by interrogating the data. This can be done by generating a display of the blockage and allowing the user to select the blockage data using a graphic data input device such as a computer mouse or stylus. The invention can then analyze the data of the first data set that corresponds to the location of the blockage. If a bright spot was shown in the first data set where a blockage is shown in the final data set, then the blockage can be identified as likely being caused by calcification. Thus, in the present invention, blockages can be more reliably characterized than they were in prior systems.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 10A is a schematic diagram of a two-dimensional array of integer numbers used to model a slice of data values.

FIG. 10B is a two-dimensional array of integers representing local neighborhood row maxima computed using the rolling buffer process of the invention.

FIG. 10C is a two-dimensional array of integers representing local neighborhood slice maxima computed using the rolling buffer process of the invention.

DETAILED DESCRIPTION OF THE INVENTION

Figure 1:
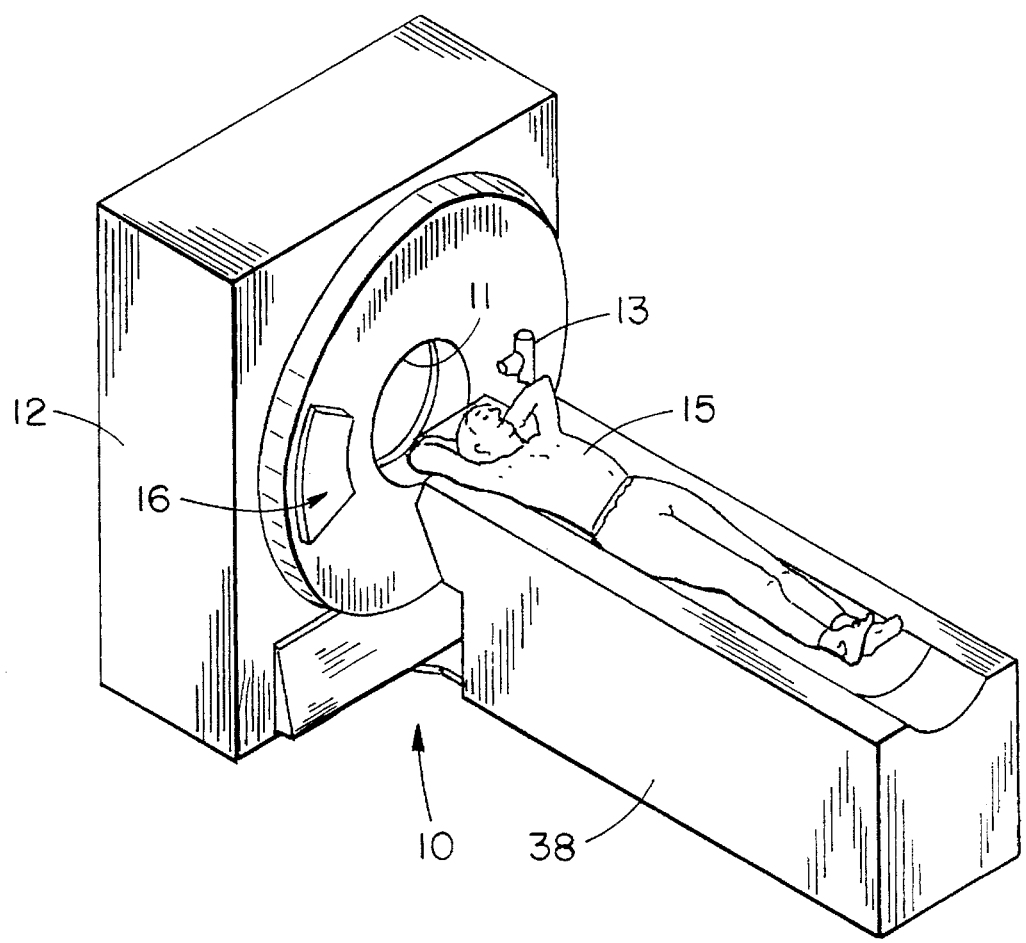
FIG. 1 is a pictorial view of a CT system in which the present invention can be implemented.
Figure 2:
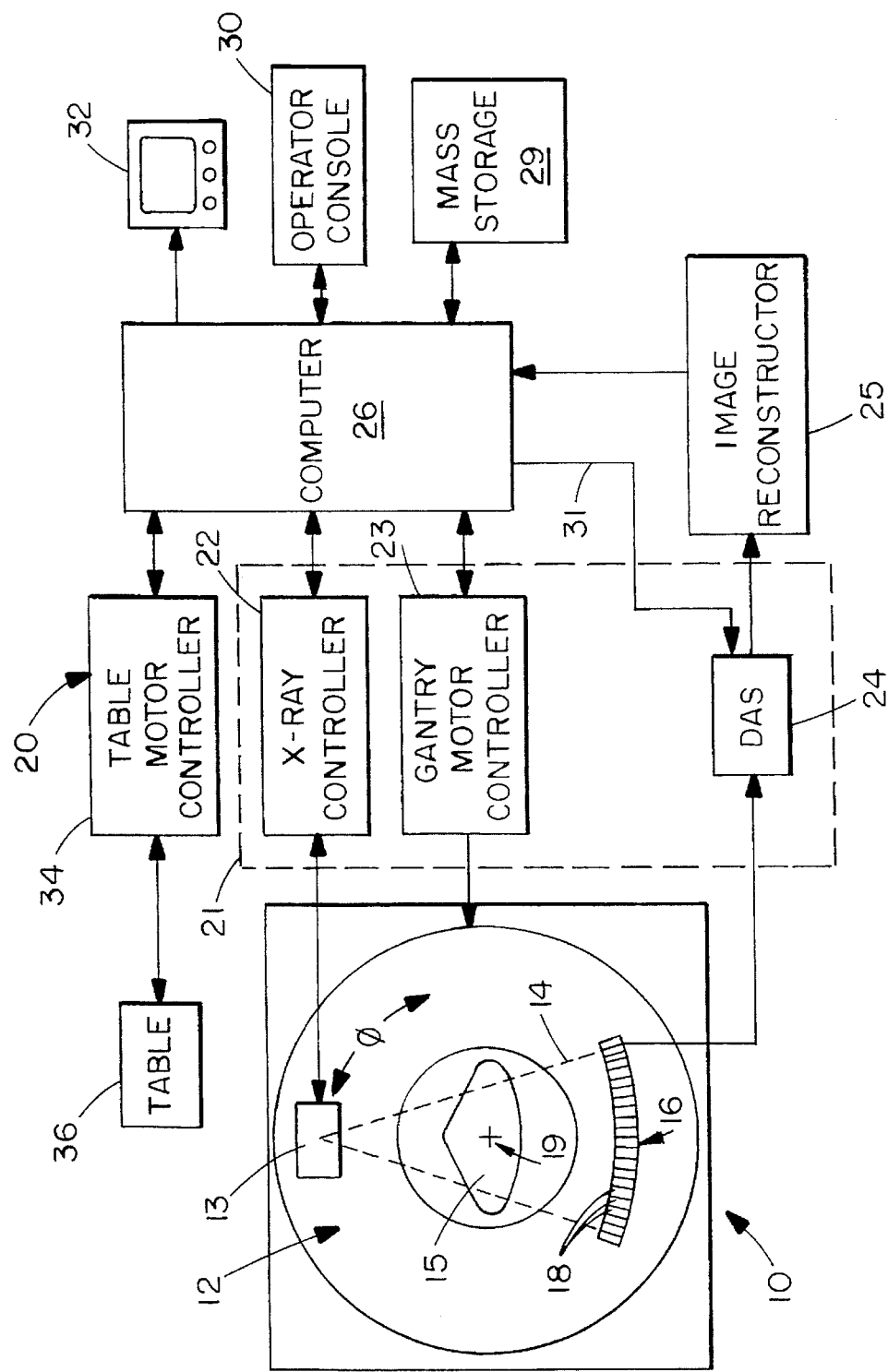
FIG. 2 is a schematic block diagram of one preferred embodiment of a CT system in which the present invention can be implemented.

Referring to FIGS. 1 and 2, a computed tomography (CT) imaging system 10 includes a gantry 12 which includes an x-ray source 13 oriented to project a fan beam of x-rays 14 through an image object such as patient 15 to detector array 16. The detector array 16 is formed by a number of detector elements 18 which together detect a projected image resulting from the transmission of x-rays through the image object 15. The gantry 12 and the components mounted thereon rotate about a center of rotation 19 normally located within the patient 15.

A controller 20 of the CT system 10 has gantry associated control modules 21 which include an x-ray controller 22 which provides power and timing signals to the x-ray source 13, a gantry motor controller 23 that controls the rotational speed and position of the gantry 12, and a data acquisition system (DAS) 24 which samples projection data from detector elements 18 and converts the data to digital words for later computer processing.

The DAS 24 filters, amplifies, digitizes and otherwise conditions the signal from each detector element 18. However, a single or a small number of such digitizing circuits can be provided with the individual signals from the detector elements 18 being time division multiplexed into that circuit. A data output from the DAS 24 is connected to image reconstructor 25 which receives sampled and digitized projection data from the DAS 24 and performs high speed image reconstruction.

The x-ray controller 22 and the gantry motor controller 23 are connected to a computer 26 which provides processing data and control signals to DAS 24 via buses 31. The computer 26 receives commands and scanning parameters via an operator console 30 that has a cathode ray tube display and keyboard which allows the operator to enter parameters for the scan and observe the reconstructed image and other information from the computer. The computer 26 can also be used to execute instructions to perform the motion-compensated target tissue image generation of the invention. A mass storage device or memory 29 provides a means for storing operating programs for the CT imaging system, as well as image data sets used to generate the final image data set of the target tissue in accordance with the invention. A separate high resolution video monitor 32 is provided to display the reconstructed image of the patient 15.

The memory and computer or processor used to generate and store the final image data set of the target tissue can also be separate from the CT system 10. In that configuration, the system 10 generates the image data from separate scans and passes the data to the separate processor and memory for processing in accordance with the invention.

Alternatively, magnetic resonance imaging (MRI) can be used to generate the paired image data sets. The imaging target, commonly a patient, is placed in a magnetic field which has an adjustable component (gradients) to change the spatial dependents of magnetic field strength. Radio waves received by the target radiate back by an excitation process at frequencies proportional to the magnetic field strength. A Fourier transform converts the received frequencies to a map of the magnetization in the target region. Additional gradients and/or radio waves may be applied to reduce magnetization from moving blood.

Thus, two data sets representing images are generated, one in which target tissue such as blood vessels are dark and one in which vessels are bright. This can be accomplished without injection of a contrast agent, but also can be made by injecting a contrast agent. It should be noted that contrast enhancement can also result in target tissue being rendered darker than background tissue. The present invention is also applicable to that case. The detailed description contained herein refers to contrast enhancement as resulting in higher-intensity image pixel values as an illustration and not as a limitation.

Figure 3:
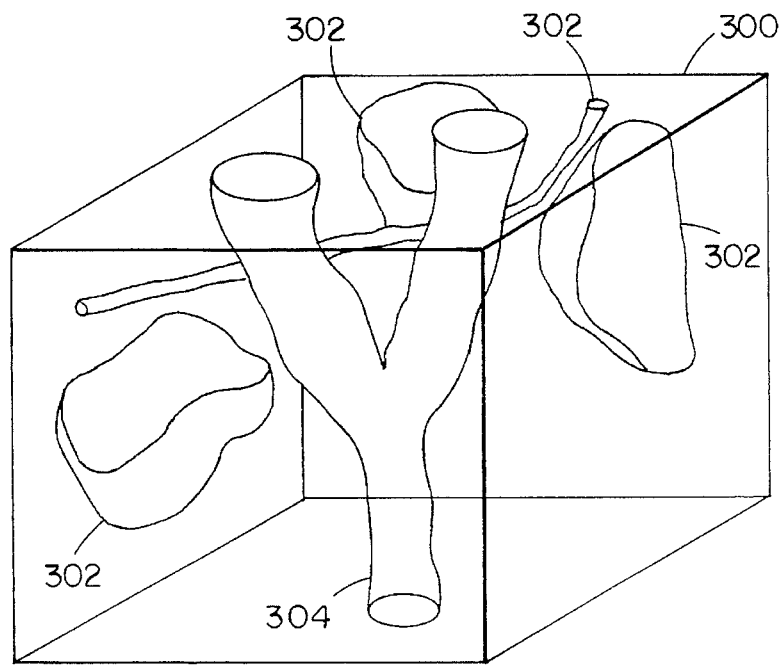
FIG. 3 is a schematic perspective pictorial view of an image of a region of tissue represented by an image data set generated during a first scan of the region.
Figure 4:
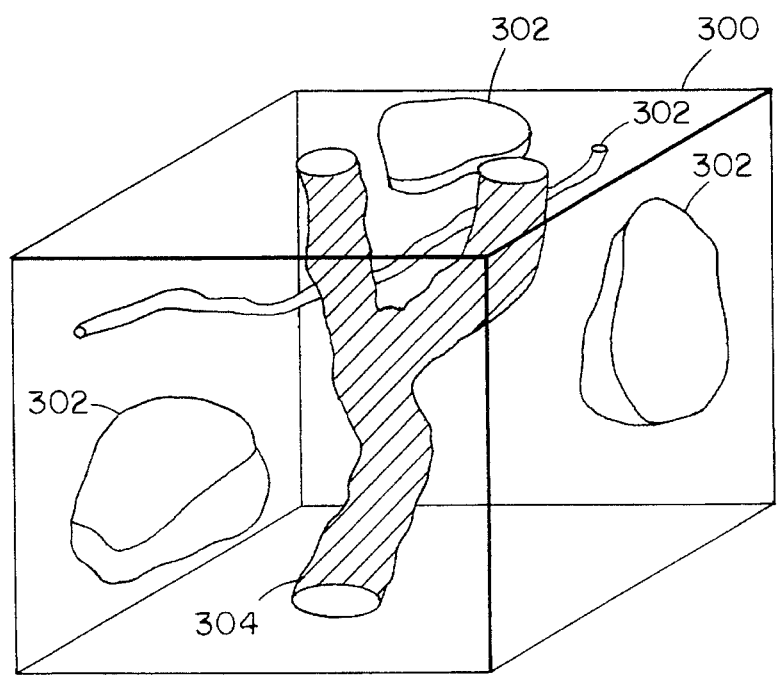
FIG. 4 is a schematic perspective pictorial view of an image of the same region of tissue as in FIG. 3 represented by an image data set generated during a second scan of the region.
Figure 5:
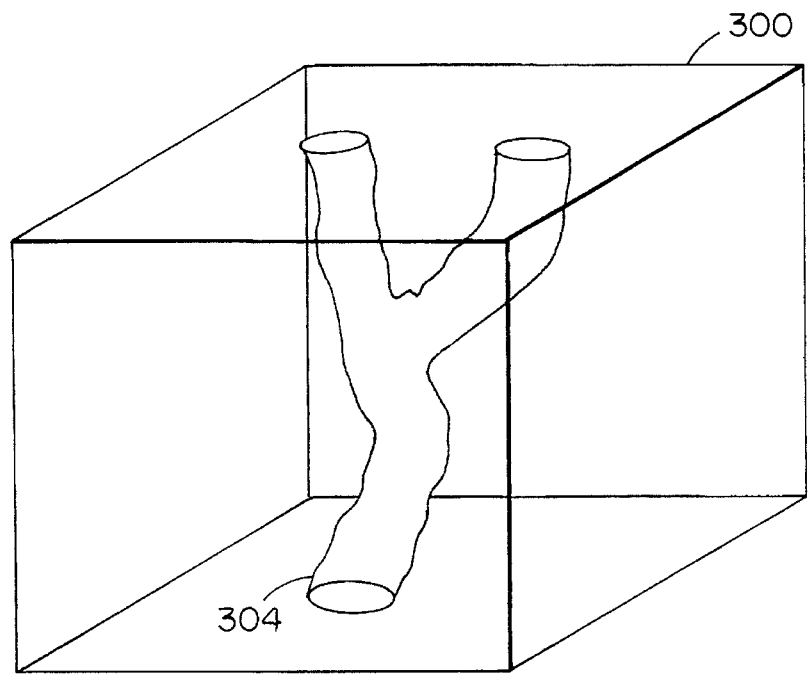
FIG. 5 is a schematic perspective pictorial view of the region of tissue of FIGS. 3 and 4 represented by an image data set generated in accordance with the image generation process of the invention showing the region of tissue with background tissue removed from the image.

FIGS. 3–5 are schematic pictorial views depicting the image data set generation process of the invention. Each figure depicts the same region of tissue 300 for which an image data set is to be generated. FIG. 3 shows the region as represented by the first image data set. The region includes background tissue 302 and target tissue 304. In this particular example, the target tissue 304 is a blood vessel shown at a branch of the vessel. FIG. 4 depicts the image represented by the second image data set of the same region of tissue 300 obtained after the contrast of the target tissue 304 has been enhanced. The second image data set also includes data representing the same background tissue 302. In FIG. 4, the target tissue 304 is shown shaded to illustrate that its contrast has been enhanced. It should also be noted from FIG. 4 that the background tissue 302 and target tissue 304 have undergone various forms of movement including compression, stretching, rotation, shifting, etc.

FIG. 5 illustrates an image of the same region of tissue 300 represented by the final data set generated by the image generation process of the invention. All that remains in the final data set are data values representing the target tissue 304 represented as it was in the second image data set illustrated in FIG. 4. The final data representation depicted in FIG. 5 can provide an image of the target tissue 304 at the position and configuration to which it had moved when the second image data set was generated. The background tissue 302, which had also undergone various movements, has been removed from the final image data set. To create the data set that represents the image of FIG. 5, the system and process of the invention identify data representative of background tissue 302 and remove it from the final data set and identify data representative of the target tissue 304 and preserve it for the final data set, despite the fact that both the background tissue and target tissue can move to different locations and assume different configurations and shapes.

Figure 6:
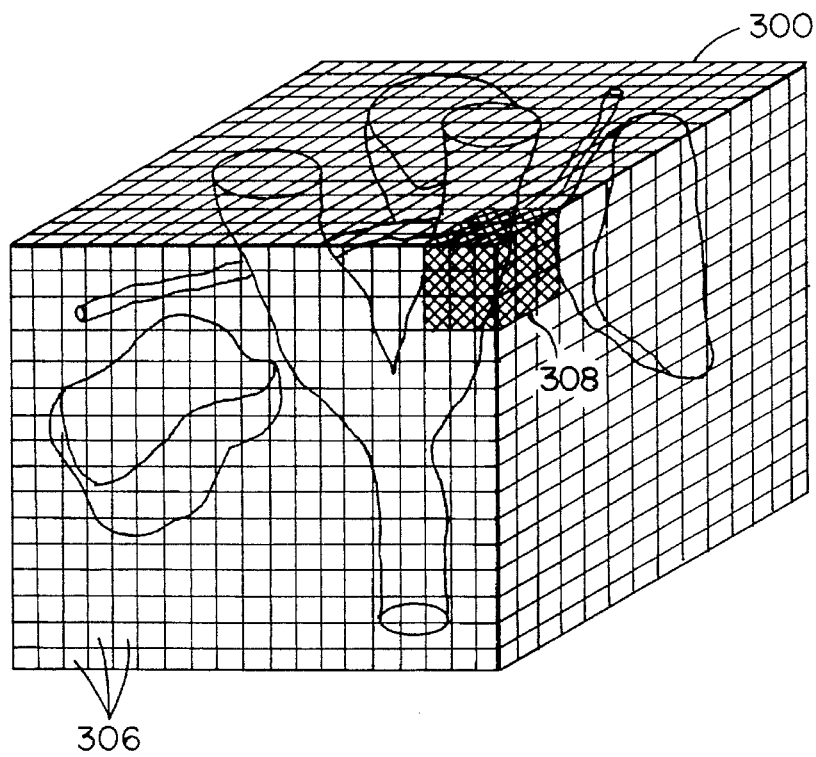
FIG. 6 shows the region of tissue of FIG. 3 with a three-dimensional pixel pattern superimposed over the image.
Figure 7:
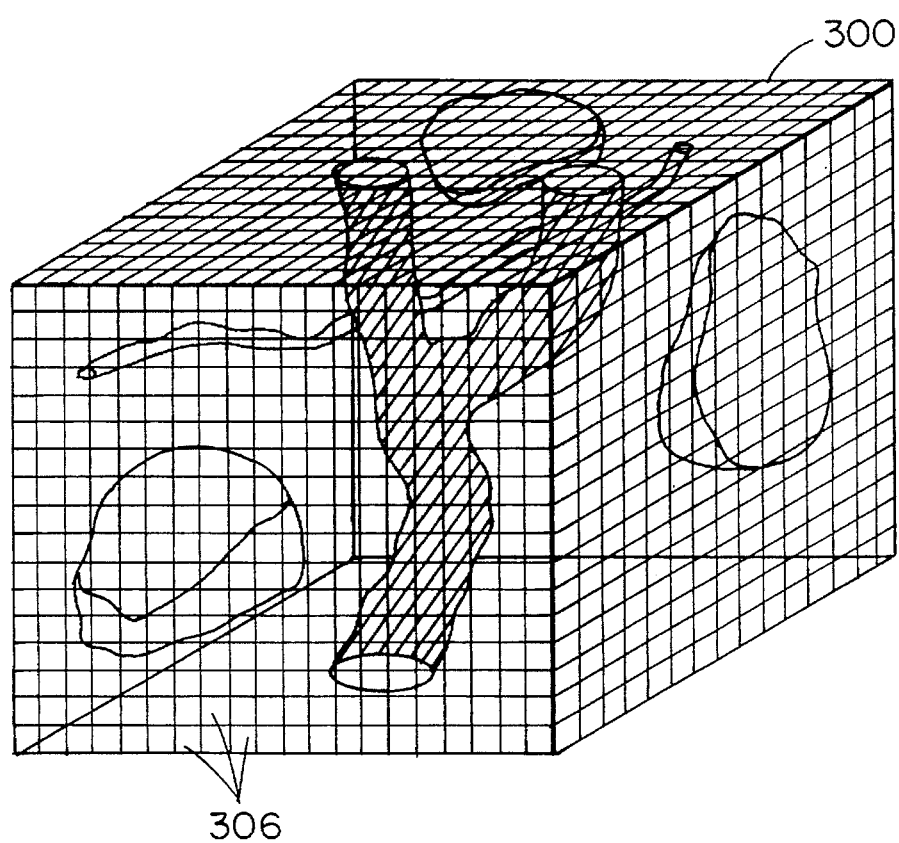
FIG. 7 shows the region of tissue of FIG. 4 with a three-dimensional pixel pattern superimposed over the image.

FIGS. 6 and 7 are schematic pictorial views of the region of tissue 300 for the first image data set and the second image data set, respectively. FIGS. 6 and 7 are the same as FIGS. 3 and 4, respectively, except that each has been overlayed with a three-dimensional grid depicting an array of sections 306 of tissue distributed throughout the region 300, each section 306 being represented by a pixel data value.

As shown in FIG. 6, the first image data set can be viewed as the union of multiple three-dimensional neighborhoods of three-dimensional sections 306 of tissue, each of which is represented by a pixel value. In FIG. 6, a single preferred neighborhood 308 is shown in cross-hatched shading. This preferred neighborhood 308 includes twenty-seven pixel values representing twenty-seven small volumes 306 of tissue effectively geometrically arranged in a cube shape, with twenty-six neighborhood pixel values representing twenty-six sections 306 of tissue surrounding the central section pixel value to which the neighborhood 308 is assigned. It should be noted that a cubic shape is chosen for ease of illustration. Other neighborhood shapes, such as spheres and rectangular solids, can also be used.

In the embodiment shown in FIG. 6, each neighborhood includes twenty-six pixel values m arranged in the cube shape surrounding a central pixel value n. Each neighborhood is effectively assigned a data value $N_1$ (n) which can be a vector or scalar, depending upon the image attribute being used to perform the image data discrimination process. For example, in one preferred embodiment, the vector $N_1$ (n) includes a value component equal to the intensity of the pixel value m within the neighborhood that has the highest intensity and a direction component indicating the location of the pixel m relative to the central pixel n. In another embodiment, the value assigned to $N_1$ (n) is a vector defining the pixel value intensity gradient for the central pixel value n of the neighborhood. In this embodiment, the gradient vector has a magnitude indicating the highest-intensity pixel value in the neighborhood and a direction component indicating the direction of highest intensity change. In other embodiments, the value assigned to $N_1$ (n) defines statistical moments for pixel value intensities within the neighborhood. For example, $N_1$ (n) can represent the mean pixel intensity value and/or the pixel intensity standard deviation, variance, etc., for the neighborhood.

FIG. 7 depicts the grid of sections 306 of tissue represented by the pixel values of the second image data set. In a preferred embodiment, each pixel value n of the second image data set is assigned a value $V_2$ (n). In one preferred embodiment, $V_2$ (n) represents the intensity of the pixel value n. In that embodiment, the value $N_1$ (n) assigned to each neighborhood in the first image data set can be the highest pixel intensity value within the neighborhood. In that case, each pixel value $V_2$ (n) of the second image data set is compared to its corresponding maximum-pixel-intensity value $N_1$ (n) in the first image data set. As described below in detail, this comparison between pixel values in the second image data set and neighborhoods in the first image data set yields a final data set for the target tissue which compensates for movement of the tissue between generation of the first and second image data sets.

In another embodiment, $V_2$ (n) is compared to each of the pixel intensity values in the neighborhood $N_1$. A pixel value $N_1$ (m) is identified as being the value within the neighborhood $N_1$ which has the closest intensity match to $V_2$ (n). The position m can be an actual discrete pixel location or it can be obtained by interpolating intensity values between actual pixels. When the best match pixel intensity value is found for $V_2$ (n), a pairing vector assigned to $V_2$ (n) is generated. One data item stored in the pairing vector is a collection of direction data indicating the difference in position between the location n and the location m. Another data value stored in the pairing vector is the difference in intensity observation or intensity error between the pixel locations n and m.

In this embodiment, the complete comparison process involves scanning through all of the pixel n values of the second image data set and comparing their values $V_2$ (n) to their corresponding neighborhoods $N_1$ (n) of the first image data set and generating a pairing vector for each pixel n value based on the best match pixel value in the neighborhood $N_1$ (n). The result of the comparison is a pairing vector space in which each pixel value of the second image data set is assigned a pairing vector. Alternatively, the comparison may be computed from summary data estimates.

The pairing vectors contain the information used to distinguish target tissue pixel values from background tissue values. The error data of each pairing vector is compared to a threshold. If the error value exceeds the threshold, then the data value of the second data set that is associated with the error value is classified as representing contrast-enhanced target tissue. If the error value is below the threshold, then the value is classified as background data. For the background values, the displacement data of their pairing vectors indicates the amount of movement the tissue that they represent underwent between acquisition of the two image data sets.

Alternatively, two thresholds can be selected to provide the process with the added flexibility of classifying borderline values as uncertain or equivocal. These values can then be analyzed further by applying various tissue movement constraints to classify them as target or background data. Also, further analysis in the form of a consistency check can be performed on the pairing vectors of background and/or target values to ensure that they are properly classified. For example, if displacement data in adjacent background pixel pairing vectors indicate movements in opposite directions, one of the pixel values should be reclassified as target data since such movement would violate known tissue characteristics.

Figure 8:
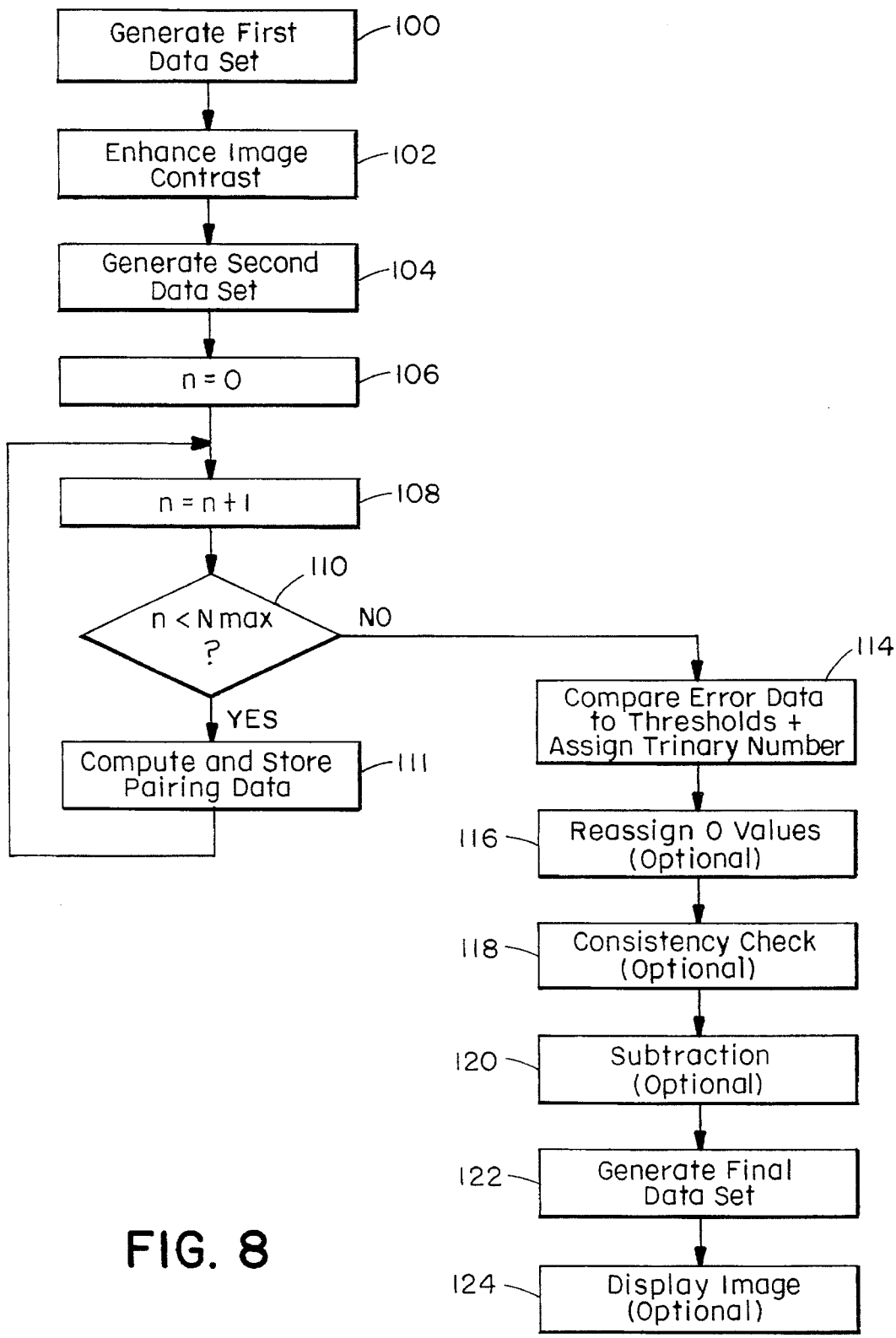
FIG. 8 is a flow diagram depicting the logical flow of one preferred image generation process in accordance with the invention.

FIG. 8 is a top-level flow diagram depicting the logical flow of one embodiment of the image data processing process of the invention. In step 100, data values are generated for the first image data set, such as by scanning the region of tissue with a CT scanner. In step 102, the image contrast between the target tissue and the background tissue is enhanced such as by injection of a vascular contrast enhancing agent. In step 104, data values are generated for the second image data set by a second scan.

In one example of obtaining the image data sets, the scanning was performed on a General Electric HiSpeed Helical CT scanner at baseline and during contrast agent injection after a preset delay to allow the contrast to fill the arterial target tissue. Typically, for a carotid artery study, the parameters for the scan can be: 140 kV, 180 mA, 40 slices at 1 mm thickness, pitch 2, delay 15 seconds and injection rate 3 cc/sec. For the circle of Willis, typical parameters can be: 140 kV, 200 mA, 40 slices at 1 mm thickness, pitch 1, delay 10 seconds and injection rate 4 cc/sec.

After the two image data sets are generated, the process of comparing the two image data sets to discriminate target tissue data values from background data values begins at step 106. An index counter variable n is initialized at step 106 and is incremented at step 108. As the loop control variable, the index n keeps track of the data value of the second data set that is presently being examined. In decision step 110, n is checked to determine if it has reached the number of data items or neighborhoods $N_{max}$ in the first data set or, equivalently, the number of data values in the second image data set. If $n<N_{max}$, then the last neighborhood or data value has not been reached, and flow continues along the "YES" branch out of decision step 110 to step 111.

In step 111, pairing the data is computed between the current data value $V_2$ (n) in the second data set and the corresponding pixel neighborhood value $N_1$ (n) in the first data set. The pairing data preferably includes the pairing vector described above which includes observation error data and pixel value displacement data.

In one embodiment, the error data is the difference in intensity between the value $V_2$ (n) of the second data set and the intensity value within the neighborhood $N_1$ that has the closest intensity value to the value $V_2$ (n), i.e., the best match pixel value. The displacement data indicates the displacement between the position of the pixel value $V_2$ (n) and the position in the neighborhood $N_1$ of the best match pixel value. As previously noted, by using interpolation, a best match pixel value and, hence, corresponding error and displacement data, can be calculated for positions between the discrete pixel value locations of the neighborhood $N_1$.

In an alternative embodiment, the value $V_2$ (n) includes a pixel intensity gradient value and/or pixel intensity statistical moments such as intensity mean and/or standard deviation. The error data of the pairing vector in these cases is again the difference between the value $V_2$ (n) and the corresponding best match value in the corresponding neighborhood of the first data set. The displacement data or vector indicates the displacement between the location of the value $V_2$ (n) and the location of the best match value in the corresponding neighborhood.

After pairing data is thus computed, flow returns to step 108 where n is again incremented and is checked again in step 111 to determine if all data has been paired. When n reaches the maximum $N_{max}$, the process proceeds along the "NO" branch out of decision step 110 to step 114 where the pairing data generated and stored in step 111 is analyzed to distinguish target tissue values from background tissue values.

In one embodiment, in step 114, each data value of the second image data set is identified as being representative of target tissue or of background tissue or as yielding an uncertain or equivocal classification. Each value is assigned a trinary digit (−1, 0 or +1) depending upon this classification. Background values are labeled −1, target values are labeled +1 and uncertain values are labeled 0.

To make the classification, the error value of each pairing vector is preferably compared to two predetermined thresholds, a lower threshold and an upper threshold. If the error value of a pairing vector is below the lower threshold, then the pixel value of the second data set associated with that pairing vector is determined to be representative of background tissue since it is present in both data sets as indicated by the low error value in its pairing vector. Accordingly, it is assigned a −1 trinary value. If the error value exceeds the upper threshold, then it is concluded that the corresponding pixel value appears only in the second image data set and is therefore representative of contrast-enhanced target tissue. The value is then assigned a +1 trinary number. Values for which the error falls between the lower and upper thresholds are classified as uncertain or equivocal and are assigned a trinary number of 0. Step 114 results in an array of trinary digits, each assigned to a data value of the second image data set.

In step 116, an optional reanalysis process can be performed to reassign 0 values as either +1 or −1. Various criteria can be applied upon reanalysis to determine whether an uncertain value should be classified as target or background. One criterion applied is consistency within regions of pixel values. That is, if a single 0 appears in a large region containing all −1 s or +1 s, then, depending upon the type of tissue being imaged, it may be desirable to change the 0 to the other value in the region, i.e., −1 or +1. A 0 can also be reclassified as a +1 to indicate target tissue if the displacement vector of an adjacent value points in the direction opposite to the displacement vector of the 0 value. These vectors would indicate impossible tissue movement and, therefore, that the 0 data value is more likely associated with contrast-enhanced target tissue that was not present in the first image data set. Zero values can also be reclassified as +1 if they establish connectivity between other +1 values. This can be helpful where an image is to be generated of a long feature such as a blood vessel. If two running links of +1 values indicating contrast-enhanced blood vessels are interrupted by a single 0 value, it can be useful to reclassify the 0 as a +1 to create a connection between the two +1 strands of data.

After or instead of the optional reassignment step 116, an optional consistency check can also be performed in step 118. The consistency check involves reprocessing the trinary value mask or array to determine if the mapping of target tissue values and background tissue values is consistent with actual known physical tissue characteristics.

For example, the consistency check of step 116 can include analyzing the displacement vectors associated with each of the data values of the second data set. If any adjacent −1 locations have displacement vectors pointing in opposite directions, it is likely that one of the values should actually have been classified as +1, that is, as representing target tissue, since it is unlikely that adjacent pieces of tissue would move in opposite directions. The data values in the regions surrounding the inconsistency are analyzed to isolate one or more pixel values that are inconsistent with the surrounding region. These inconsistent values are then reclassified as +1 target values. Regional consistency can also be checked independent of displacement data for the data values. For example, if a single −1 value appears in a region of +1 values then, depending upon the type of tissue being imaged, it may be helpful to reclassify the −1 value as a +1 to ensure regional consistency.

An optional subtraction process can be performed on the data set in step 120 to further enhance the quality of the resulting image. Subtraction is performed to correct the pixel value intensity of a target tissue value to compensate for the portion of the intensity value contributed by the background tissue at the location represented by the data value.

To illustrate, before enhancement of the target tissue, the data values representing the region of tissue of the first image data set represent only background tissue which can include soft tissue, bone, etc. After enhancement, the enhanced target tissue is effectively layed over the background tissue of the region. Each intensity for the data values of the target tissue locations is essentially the sum of the background tissue value intensity and the target tissue value intensity at each location.

For most imaging applications, it is acceptable to present an image based on data values with these summed background and target pixel intensity values. In most applications, an accurate visual representation of the tissue can be presented, albeit artificially brightened by the background contribution. In those applications, the new data set generated as described above is used to present an image of the target tissue. However, in some applications, it is more useful to obtain an accurate representation of the amount of target tissue enhancement such that an image of only the enhancement, independent of background, can be presented. In such applications, the invention can subtract the contribution of the background tissue to obtain that portion of the target value attributable to only target tissue. In one embodiment, the subtraction process 120 calculates for each value location identified as representing target tissue the difference between the intensity of the target value at the location and an interpolated background intensity value at the derived corresponding location in the first image set. That difference is used as the intensity for the data value in the new subtracted data set.

The adjusted subtracted data values can replace the corresponding data values that were present in the target data set before subtraction. Alternatively, an entirely new subtracted data set can be generated such that both an image without subtraction (enhancement with background) and an image with subtraction (enhancement only) can be generated.

To accurately perform the subtraction calculation, the process must allow for movement of the data value location between acquisition of the two data sets so that the correct background intensity value can be subtracted. To that end, in one preferred embodiment, each object target tissue value of the second data set is processed separately by analyzing the pairing data for the background pixel values near the object target value. The nearby background values are preferably selected by analyzing the values surrounding the object target value in, for example, eight different preferably equally spaced angular directions radiating away from the object target pixel value. In each of the eight directions, the distance from the object target value to the first background value detected is recorded along with the displacement value recorded in the pairing vector for that background pixel value. Each of the eight displacements is weighted by the inverse of its corresponding distance from the object target value, and a weighted average displacement is computed. In the resulting average displacement, pixel displacements close to the object target value are weighted more than displacements for pixels further away.

The average pixel displacement is a good approximation for the amount of displacement that the background tissue at the object target tissue location underwent between acquisition of the two image data sets. This average displacement is applied to the image data sets to identify the location in the first image data set that corresponds to the object target value location in the second image data set, and a background intensity value that corresponds to that location is determined. In the case of a fractional average displacement, this background intensity value is interpolated from nearby discrete background pixel data values. The background intensity data is subtracted from the intensity data for the object target value in the second image data set. The resulting difference is stored with the new object target value as its intensity.

An alternative subtraction process performed in step 120 involves computing a weighted average background intensity for each target value (as opposed to the weighted average displacement described above) and subtracting each average background intensity value from the intensity value of its corresponding target value. As in the weighted average displacement subtraction approach described above, for each object target value, the distance between the object target value and the nearest background value in each of eight equally spaced angular directions is preferably computed. In this weighted intensity approach, the intensity value stored for each of those eight background values is weighted by the inverse of its distance from the object target value, and a weighted average background intensity value using the weights is computed. This serves as an alternative estimate of the background instead of the method above in which the displacement vector from these locations was interpolated and then applied to the first data set. The average background intensity value thus computed is taken to be the intensity of the background tissue at the object target value location. It is subtracted from the intensity value of the object target value. The resulting difference is stored as the intensity of the object target value in the new data set.

The new or final image data set is generated in step 122 and a resulting image can optionally be displayed in step 124. Various criteria can be applied to form the new data set and generate an image therefrom. The new data set can simply be the set of all values assigned a +1 trinary number during step 114 without any subsequent reassignment (step 116), consistency check (step 118) or subtraction (step 120). All the 0 trinary values can also be added to this new data set. A new image data set can also include all +1 values and all 0 and −1 values that border a +1 value. This can be done to ensure that phenomena such as the partial volume effect at the boundary between target tissue and background tissue do not degrade the image. Where the subtraction step 120 was carried out, the new image data set can include all points in the second data set in which the mask value is +1 after subtracting the corresponding interpolated background value. Inclusion of the immediate neighbors also improves gradient computations which estimate the surface and lighting conditions for rendering the data as a three-dimensional object. Virtually any combination of these criteria can be applied to the data to produce an image of the target tissue. Other criteria can be developed and implemented as users become accustomed to the types of data sets that produce useful results in various applications.

In one embodiment, comparisons proceed very quickly because neighborhoods in the first data set need not be reexamined in their entirety for each data value of the second data set. Instead, the invention uses a rolling buffer approach in which the first data set is preprocessed to identify neighborhood summary data values, and then the data values of the second data set are compared to their corresponding neighborhood summary data values of the first data set. Summary data values can include, for example, the highest pixel intensity in the neighborhood or in one of plural data slices in the neighborhood.

Figure 9:
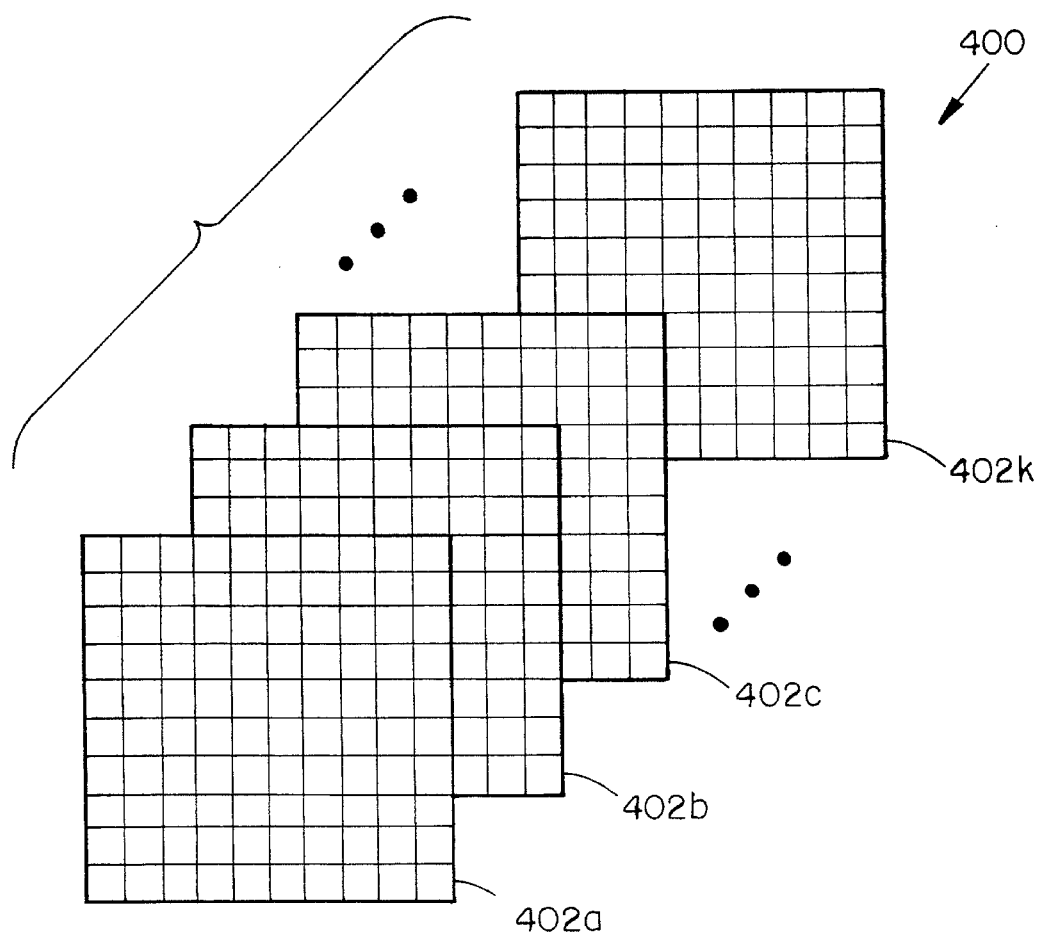
FIG. 9 is a schematic diagram depicting a stack of slices of data values in accordance with the present invention.

One preferred rolling buffer comparison approach will now be described in detail with reference to FIGS. 9–10C. Referring specifically to FIG. 9, where neighborhoods of rectangular solid shape are used, each data set 400 can be viewed as a plurality of adjacent stacked slices 402a–402k of data, where k is the total number of slices in the data set. Each slice includes a plurality of rows and columns of data values.

FIGS. 10A–10C schematically illustrate preprocessing of a single slice 402 of a first image data set 400. FIG. 10A shows the slice 402 prior to preprocessing with a representative data value entered in each location of the two-dimensional array of rows and columns. The array includes five rows i labelled 1–5 and five columns j labelled 1–5. It will be understood that the integer digits entered at each location are intended only to illustrate the preprocessing approach used in the invention. The integer values are used only to facilitate illustration of the invention. In actual use, the values entered in the array are data values acquired by scanning the region of tissue. It will also be noted that each of the rows and columns of the data set array contains five entries, resulting in 5×5 data set slices. Again, the use of the 5×5 array facilitates description of the invention. In actual practice, the data set array is much larger; for example, it can be 256×256 or 512×512.

Each entry $e_{ij}$ in the array or slice 402 is an integer value used herein to illustrate a data value of the first image data set, where the subscripts i and j define the row and column, respectively, of the entry. For example, entry $e_{35}$ is an integer 9. In this illustration, it is assumed that each neighborhood of the first image data set is a cubic array having dimensions 3×3×3 data values. Therefore, each slice 402 contains nine data values for one slice of each of nine neighborhoods. That is, one neighborhood includes the nine entries $e_{11}=1$, $e_{12}=2$, $e_{13}=3$, $e_{21}=2$, $e_{22}=4$, $e_{23}=7$, $e_{31}=4$, $e_{32}=3$ and $e_{33}=6$, This upper left neighborhood, like all of the other neighborhoods, includes nine data values in each of two other slices behind the slice 402 (not shown) for a total of twenty-seven data values in the neighborhood. Another neighborhood, the center neighborhood, which overlaps the above neighborhood, includes data entries $e_{22}=4$, $e_{23}=7$, $e_{24}=1$, $e_{32}=3$, $e_{33}=6$, $e_{34}=1$, $e_{42}=4$, $e_{43}=1$ and $e_{44}=1$. Thus, nine neighborhoods are represented by the twenty-five entries in the 5×5 array or slice 402.

The preprocessing first involves analyzing each row of the slice 402 one neighborhood, i.e., three values, at a time to identify neighborhood row summary data. FIG. 10B illustrates the results of the row preprocessing procedure. Referring to FIGS. 10A and 10B, assuming 3×3×3 neighborhoods, each five-entry row of slice 402 is analyzed one neighborhood (three entries) at a time and the summary data for that neighborhood row (three of the five values of the row), e.g., the maximum data value of the neighborhood row, is entered in a corresponding location of the array of FIG. 10B. For example, in the first step, the three entries $e_{11}$, $e_{12}$ and $e_{13}$ of slice 402, which make up one neighborhood row in FIG. 10A, are compared to identify the maximum value of the three. The result (3) is entered as entry $e_{12}$ in the array of FIG. 10B as the local neighborhood row maximum, that is, the maximum value of the three values in the top row of the top left neighborhood in slice 402.

In the next step, entries $e_{12}$, $e_{13}$ and $e_{14}$ of slice 402 are analyzed for the next adjacent neighborhood. This analysis consists of first determining whether the entry $e_{11}=1$ dropped from the last neighborhood was the local maximum of the last neighborhood. In this case it was not. If it had been, then a new maximum of $e_{12}$, $e_{13}$ and $e_{14}$ would be computed. Because $e_{11}$ was not the maximum, the new value at entry $e_{14}$ (5) is compared to the previous local maximum value (3). Since it is larger than the previous maximum value, then it is identified as the local row maximum for this new second neighborhood and is entered as the corresponding entry $e_{13}$ in FIG. 10B. Depending on the size of the neighborhoods, this single-value comparison can yield considerable time and processing savings.

In the next step, entries $e_{13}$, $e_{14}$ and $e_{15}$ of array 402 of FIG. 10A are analyzed. First, it is determined that the value $e_{12}=2$ was not the maximum value of the previous neighborhood. Next, the new value at entry $e_{15}$ (2) is compared to the previous maximum (5). Since it is lower than the previous maximum, then the previous maximum is entered as the local row maximum of this third neighborhood as $e_{14}$ of the array in FIG. 10B. This process repeats for the remaining four rows of the slice 402 in FIG. 10A to complete the entries of row maxima for all of the neighborhoods in FIG. 10B.

Next, column preprocessing similar to the row preprocessing described above is performed on the array of FIG. 10B to produce the array of FIG. 10C. In the first step of column processing, entries $e_{12}$, $e_{22}$ and $e_{32}$ of the array of FIG. 10B are compared to identify a local neighborhood column maximum. The result (7) is entered as the corresponding entry $e_{22}$ of the array in FIG. 10C. Next, entries $e_{22}$, $e_{32}$ and $e_{42}$ of the array of FIG. 10B are analyzed. It is first determined that the dropped entry $e_{12}$ (3) was not the local column maximum value of the previous neighborhood. Next, the new entry $e_{42}=4$ is compared to the previous maximum (7). Since the new value is not larger than the old value, then the old value is entered as the new local neighborhood column maximum as entry $e_{32}$ of the array of FIG. 10C. Next, entries $e_{32}$, $e_{42}$ and $e_{52}$ of FIG. 10B are analyzed. Since the dropped value $e_{22}=7$ was the local column maximum for the previous neighborhood, then the three new entries are analyzed to identify their maximum. The result (6) is entered as $e_{42}$ of the array in FIG. 10C. This process continues for the remaining two columns of the array of FIG. 10B to complete the array of FIG. 10C.

The resulting array of FIG. 10C contains the nine local slice maximum values within the slice 402 for the nine neighborhoods that contain data values from slice 402. Each neighborhood slice maximum in the array in FIG. 10C is located at the central location within the slice 402 of its corresponding neighborhood.

This process is repeated for each slice in the data set 400 to identify all of the local slice maxima for all of the neighborhoods. In the case of 3×3×3 rectilinear neighborhoods, this results in each three-dimensional neighborhood being associated with three local slice maxima, i.e., one for each slice in the neighborhood.

In one embodiment, these three local slice maxima for each neighborhood are compared to each other to identify a neighborhood maximum for each neighborhood. The comparison process of the invention then proceeds as each data value of the second image data set is compared to its corresponding neighborhood maximum value to classify the data value of the second image data set as being representative of target tissue or background tissue or as being uncertain in accordance with the foregoing description.

In another embodiment, the comparison of the three local slice maxima to identify a neighborhood maximum is dispensed with. Instead, the comparison and classification processes are performed directly on the three local slice maxima. Each data value of the second image data set is compared to the three slice maxima of its corresponding neighborhood of the first image data set computed as described above.

It will be appreciated that this "rolling buffer" approach saves a substantial amount of computation resources. The number of calculations performed using the approach is far less than the number of calculations that would be performed if each data value of the second data set were compared to all of the values in its corresponding neighborhood of the first data set.

The system and method of the invention are not limited to generating data sets for tissue with enhanced image contrast. In fact, the approach described above of comparing data values of one data set to neighborhoods of data values of another data set can be used in several different applications.

For example, the invention can be used to identify tissue by comparing a representative data set of the tissue to a previously compiled image data set in a stored atlas of normal anatomy. Each entry in the atlas of normal anatomy is a data set that represents an image of a particular region of normal tissue. In this application, the second data set described herein is a data set obtained from an object or region of tissue that is to be identified by associating it with an entry in the atlas. This data set can be compared to those of the atlas to produce a new or difference data set indicative of the difference between the unknown data set and those of the atlas. An atlas data set entry that exhibits a small difference and, therefore, a close similarity, to the unknown data set is associated with the unknown to identify it.

The approach of the invention allows for differences in view angle, tissue movement, intensity variations, etc. between acquisition of the atlas data set entries and the unknown data set. The displacement vectors enable a direct transfer of anatomic labels from the atlas of normal anatomy to the new image data. As a result, a viewer can request a particular label such as "Circle of Willis" or other anatomic label and a computer can render everything else translucent, highlighting the named target. Furthermore, all points that do not fit and are thus labelled +1 in accordance with the foregoing description, are of particular interest because they are points that are not found among all the cases of normal anatomy. This would be expected, for example, if the new image data has a tumor. Such points can be automatically highlighted and viewed in various ways in order to identify abnormalities.

A similar application involves a pathology library, in which image sets for various pathologic samples are stored. A new data set corresponding to a region of tissue that is to be characterized is selected. That data set is compared to the pathology library to classify the tissue according to the closest matching pathologic example in the library. Recall that matching can be achieved by comparing texture as well as intensity and other measures such as fractile dimension. The closest match to a tumor, for example, will identify the most similar entry in the pathology library whose tissue type and response to various treatments is known.

In another application of the invention, multiple data sets are acquired and compared for a single patient over time. For example, where the growth of a tumor is to be tracked over time, data sets representing the tumor can be obtained periodically, for example, every month. Each newly acquired data set can be compared to one or more of its predecessors to identify expansion and contraction of the tumor tissue, by assessment of the displacement vectors.

In another application of the invention, target tissue in the second data set is not identified based on whether it was present in the first data set. Instead, a target region of tissue can be defined by the user such as by computer input. The identified target tissue region of the second data set can then be compared to corresponding neighborhoods in the first image data set in accordance with foregoing description. This enables the user to track movement in the selected target tissue region. Such motion tracking can generate, for example, a strain map of the heart as it moves during cardiac cycle.

It is noted that the foregoing description of the process of the invention described data comparison between data sets occurring in a serial fashion. However, the process of the invention can also be carried out in a parallel processing system. In such a system, multiple calculations and/or comparisons can be carried out simultaneously in parallel by separate processing units. In this fashion, generation of the final data set can be carried out very efficiently, thus allowing an image of the target tissue to be generated very quickly.

While this invention has been particularly shown and described with references to preferred embodiments thereof, it will be understood by those skilled in the art that various changes in form and details may be made therein without departing from the spirit and scope of the invention as defined by the appended claims.

The invention claimed is:

1. A method of generating a representation of target tissue in a region of tissue comprising:

generating a first representation of the region of tissue;

generating a second representation of the region of tissue;

forming an association between each of a plurality of data values of the second representation and a corresponding neighborhood of data values of the first representation;

comparing data values of the second representation with data values of respective associated neighborhoods of the first representation to distinguish target tissue data values of the second representation from background tissue data values of the second representation; and generating the representation of the target tissue using the target tissue data values of the second representation.

2. The method of claim 1 further comprising enhancing contrast in the second representation between the target tissue and the background tissue in the region of interest.

3. The method of claim 1 wherein each of the first and second representations is generated by performing a scan of the region of tissue with a CT imaging system.

4. The method of claim 1 wherein each of the first and second representations is generated by performing a scan of the region of tissue with an MRI imaging system.

5. The method of claim 1 wherein a data value of the first representation comprises summary data for a neighborhood of data values in the first representation.

6. The method of claim 5 wherein the summary data for a neighborhood of data values includes maximum pixel intensity information for all of the pixels represented by data values in the neighborhood.

7. The method of claim 5 wherein the summary data for a neighborhood of data values includes minimum pixel intensity information for all of the pixels represented by data values in the neighborhood.

8. The method of claim 5 wherein the summary data for a neighborhood of data values includes information regarding intensity statistical moments for pixels represented by the data values in the neighborhood.

9. The method of claim 1 wherein a partial volume data value of the second representation that represents both background tissue and target tissue is used to generate the representation of the target tissue.

10. The method of claim 1 wherein the step of comparing comprises generating an error value defined by a difference between a data value of the second representation and a data value of the first representation.

11. The method of claim 10 wherein the step of generating the representation of the target tissue comprises computing at least one curve fit to error values associated with data values of the second representation.

12. The method of claim 1 wherein each neighborhood of data values of the second representation represents a volume of tissue within the region of tissue.

13. The method of claim 12 wherein the volume is a rectangular solid.

14. The method of claim 1 further comprising computing a displacement between a data value of the first representation and a corresponding data value of the second representation.

15. The method of claim 1 further comprising classifying data values of the second representation as background tissue values, target tissue values or uncertain.

16. The method of claim 15 further comprising:
analyzing data values classified as uncertain; and
reclassifying uncertain data values as background tissue values or target tissue values.

17. The method of claim 1 further comprising generating an image of the target tissue from the representation of the target tissue.

18. The method of claim 1 wherein data values of the second representation are compared with data values of neighborhoods of the first representation using a rolling buffer process.

19. A method of classifying data values in a data set representative of tissue in a region of tissue comprising:
providing a first data set;
generating a second data set representative of the region of tissue;
forming an association between each of a plurality of data values of the second data set and a corresponding neighborhood of data values of the first data set;
comparing data values of the second data set with data values of respective associated neighborhoods of the first data set; and
classifying data values of the second data set according to the comparison performed during the comparing step between data values of the second data set and data values of the first data set.

20. An imaging system for generating a representation of target tissue in a region of tissue comprising:
a data collection subsystem comprising a source of radiation and a detector, said detector generating a first representation of the region of tissue and a second representation of the region of tissue;
a data processor that forms an association between each of a plurality of data values of the second representation and a corresponding neighborhood of data values of the first representation, that compares data values of the second representation with data values of respective associated neighborhoods of the first representation to distinguish target tissue data values of the second representation from background tissue data values of the second representation and that generates the representation of the target tissue using the target tissue data values of the second representation.

21. The imaging system of claim 20 wherein the second representation has enhanced contrast between the target tissue and the background tissue in the region of tissue.

22. The imaging system of claim 20 wherein the data collection subsystem comprises a CT scanning system.

23. The imaging system of claim 20 wherein the data collection subsystem comprises an MRI scanning system.

24. The imaging system of claim 20 wherein a data value of the first representation comprises summary data for a neighborhood of data values of the first representation.

25. The imaging system of claim 24 wherein the summary data for a neighborhood of data values includes maximum pixel intensity information for all of the pixels represented by the data values in the neighborhood.

26. The imaging system of claim 24 wherein the summary data for a neighborhood of data values includes minimum pixel intensity information for all of the pixels represented by data values in the neighborhood.

27. The imaging system of claim 24 wherein the summary data for a neighborhood of data values includes information regarding intensity statistical moments for pixels represented by the data values in the neighborhood.

28. The imaging system of claim 20 wherein a partial volume data value of the second representation that represents both background tissue and target tissue is used by the data processor to generate the representation of the target tissue.

29. The imaging system of claim 20 wherein the data processor generates an error value defined by a difference between a data value of the second representation and a data value of the first representation.

30. The imaging system of claim 29 wherein the data processor computes at least one curve fit to error values associated with data values of the second representation.

31. The imaging system of claim 20 wherein each neighborhood of data values of the second representation represents a volume of tissue within the region of tissue.

32. The imaging system of claim 31 wherein the volume is a rectangular solid.

33. The imaging system of claim 20 wherein the data processor computes a displacement between a data value of the first representation and a corresponding data value of the second representation.

34. The imaging system of claim 20 wherein the data processor classifies data values of the second representation as background tissue values, target tissue values or uncertain.

35. The imaging system of claim 34 wherein the data processor analyzes data values classified as uncertain and reclassifies uncertain data values as background tissue values or target tissue values.

36. The imaging system of claim 20 further comprising a display for presenting an image of the target tissue from the representation of the target tissue.

37. A method of generating an image of blood vessels in a region of tissue comprising:
scanning the region of tissue to generate a first data set for the region of tissue;
introducing a vascular contrast enhancing agent into the blood vessels in the region of tissue;
after introducing the vascular contrast enhancing agent, scanning the region of tissue to generate a second data set for the region of tissue;
forming an association between each of a plurality of data values of the second data set and a corresponding neighborhood of data values of the first data set;
comparing data values of the second data set with data values of respective associated neighborhoods of the first data set to distinguish contrast-enhanced blood vessel data values of the second data set from background tissue data values of the second data set; and generating a data set for the blood vessels using the contrast-enhanced blood vessel data values of the second data set.

38. The method of claim 37 wherein each of the first and second data sets is obtained by scanning the region of tissue with a CT imaging system.

39. The method of claim 37 wherein the step of comparing comprises generating an error value defined by a difference between a data value of the second data set and data value of the first data set.

40. The method of claim 37 wherein each neighborhood of data values of the second data set represents a volume of tissue within the region of tissue.

41. The method of claim 40 wherein the volume is a rectangular solid.

42. The method of claim 37 further comprising computing a displacement between a data value of the first data set and a corresponding data value of the second data set.

43. The method of claim 37 further comprising classifying data values of the second data set as background tissue values, blood vessel tissue values or uncertain.

44. The method of claim 37 further comprising generating an image of the blood vessels from the data set for the blood vessels.

* * * * *